United States Patent
Conley et al.

(10) Patent No.: US 6,415,175 B1
(45) Date of Patent: Jul. 2, 2002

(54) INTERFACE FOR A MEDICAL DEVICE SYSTEM

(75) Inventors: Vickie L. Conley, Woodbury; Allan T. Koshiol, Lino Lakes, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/372,157

(22) Filed: Aug. 20, 1999

(51) Int. Cl.[7] .................................................. A61B 5/04
(52) U.S. Cl. ........................................ 600/523; 600/518
(58) Field of Search ............................... 600/518, 523, 600/509; 607/5, 4, 17

(56) References Cited

U.S. PATENT DOCUMENTS

| | | | |
|---|---|---|---|
| 4,006,737 A | 2/1977 | Cherry | 128/2.06 G |
| 4,090,505 A | 5/1978 | Mortara | 128/2.06 G |
| 4,166,470 A | 9/1979 | Neumann | 128/419 PG |
| 4,172,459 A | 10/1979 | Hepp | 128/697 |
| 4,187,854 A | 2/1980 | Hepp et al. | 128/419 PG |
| 4,316,249 A | 2/1982 | Gallant et al. | 364/417 |
| 4,336,810 A | 6/1982 | Anderson et al. | 128/702 |
| 4,509,530 A | 4/1985 | Curtis et al. | 128/710 |
| 4,529,401 A | 7/1985 | Leslie, J.E., et al. | 604/131 |
| 4,549,552 A | 10/1985 | Groch et al. | 128/700 |
| 4,680,708 A | 7/1987 | Ambos et al. | 364/417 |
| 4,947,857 A | 8/1990 | Albert et al. | 128/696 |
| 4,974,598 A | 12/1990 | John | 128/696 |
| 5,012,814 A | 5/1991 | Mills et al. | 128/691 |
| 5,027,824 A | 7/1991 | Dougherty et al. | 128/702 |
| 5,046,704 A | 9/1991 | Albert et al. | 128/696 |
| 5,047,930 A | 9/1991 | Martens et al. | 364/413.04 |
| 5,050,612 A | 9/1991 | Matsumura | 128/670 |
| 5,052,395 A | 10/1991 | Burton et al. | 128/661.09 |
| 5,113,869 A | 5/1992 | Nappholz et al. | 128/696 |
| 5,299,118 A | 3/1994 | Martens et al. | 364/413.05 |
| 5,309,919 A | 5/1994 | Snell et al. | 128/697 |
| 5,311,873 A | 5/1994 | Savard et al. | 128/696 |
| 5,315,512 A | 5/1994 | Roth | 364/413.25 |
| 5,341,811 A | 8/1994 | Cano | 128/696 |
| 5,342,402 A | 8/1994 | Olson et al. | 607/5 |
| 5,487,754 A | 1/1996 | Snell et al. | 607/27 |
| 5,487,755 A | 1/1996 | Snell et al. | 607/27 |
| 5,513,645 A | 5/1996 | Jacobson et al. | 128/710 |
| 5,535,753 A | 7/1996 | Petrucelli et al. | 128/672 |
| 5,555,888 A | 9/1996 | Brewer et al. | 128/702 |
| 5,578,063 A | 11/1996 | Bocek, J.M., et al. | 607/5 |
| 5,584,298 A | 12/1996 | Kabal | 128/672 |
| 5,603,331 A | 2/1997 | Heemals, J.P., et al. | 128/696 |
| 5,613,495 A | 3/1997 | Mills et al. | 128/696 |
| 5,626,620 A | 5/1997 | Kieval et al. | 607/9 |
| 5,626,623 A | 5/1997 | Kieval et al. | 607/23 |
| 5,628,321 A | 5/1997 | Scheib et al. | 128/661.08 |
| 5,643,255 A | 7/1997 | Organ | 606/41 |

(List continued on next page.)

FOREIGN PATENT DOCUMENTS

EP 0565084 10/1993 ......... A61B/5/0452

*Primary Examiner*—Jeffrey R. Jastrzab
(74) *Attorney, Agent, or Firm*—Schwegman, Lundberg, Woessner & Kluth, P.A.

(57) ABSTRACT

A medical device system having an improved interface and method of operation that more efficiently facilitates interaction with a user. In one aspect the medical device system and method graphically displays a hierarchy of input mechanism that each correspond to a set of arrhythmic episodes having a common data characteristic, such as zone of detection of arrhythmia type. By selecting one of the input mechanisms, the user is able to quickly view detailed information of the set of arrhythmic episodes. Among other features, the medical device system also displays cardiac events in a histogram format such that the histogram has an axis representing a range of heart beat rates. According to the invention, the system scales the histogram as a function of all of the stored event in a normal view and scales the histogram as a function of a subset of the events in a magnification view, thereby allowing the user to better see the events along a portion of the histogram.

39 Claims, 8 Drawing Sheets

U.S. PATENT DOCUMENTS

| | | | |
|---|---|---|---|
| 5,647,369 A | 7/1997 | Petrucelli et al. | 128/672 |
| 5,674,249 A | 10/1997 | de Coriolis, P.E., et al. | 607/5 |
| 5,683,431 A | 11/1997 | Wang | 607/28 |
| 5,687,737 A | 11/1997 | Branham et al. | 128/710 |
| 5,697,959 A | 12/1997 | Poore | 607/32 |
| 5,716,383 A | 2/1998 | Kieval et al. | 607/9 |
| 5,716,384 A | 2/1998 | Snell | 607/30 |
| 5,722,999 A | 3/1998 | Snell | 607/32 |
| 5,724,985 A | 3/1998 | Snell et al. | 128/697 |
| 5,743,268 A | 4/1998 | Kabal | 128/691 |
| 5,749,906 A | 5/1998 | Kieval et al. | 607/9 |
| 5,749,907 A | 5/1998 | Mann | 607/27 |
| 5,772,604 A | 6/1998 | Langberg et al. | 600/518 |
| 5,788,640 A | 8/1998 | Peters | 600/483 |
| 5,792,203 A | 8/1998 | Schroeppel, E.A. | 607/30 |
| 5,792,204 A | 8/1998 | Snell | 607/32 |
| 5,817,137 A | 10/1998 | Kaemmerer | 607/59 |
| 5,833,623 A | 11/1998 | Mann et al. | 600/523 |
| 5,891,179 A | 4/1999 | Er et al. | 607/27 |
| 5,924,989 A | 7/1999 | Polz | 600/443 |
| 5,951,484 A | 9/1999 | Hoium et al. | 600/515 |
| 5,954,664 A | 9/1999 | Seegobin | 600/515 |
| 5,961,467 A | 10/1999 | Shimazu et al. | 600/485 |
| 5,974,341 A | 10/1999 | Er et al. | 607/31 |
| 6,004,276 A | 12/1999 | Wright et al. | 600/508 |
| 6,016,442 A | 1/2000 | Hsu et al. | 600/518 |
| 6,017,307 A | 1/2000 | Raines | 600/300 |
| 6,091,990 A | 7/2000 | Hsu, W., et al. | 607/5 |
| 6,289,244 B1 | 9/2001 | Conley, V.L. et al. | 607/27 |
| 6,289,248 B1 | 9/2001 | Conley, V.L., et al. | 607/59 |
| 6,301,503 B1 | 10/2001 | Hsu, W., et al. | 607/30 |

INTERFACE FOR A MEDICAL DEVICE SYSTEM

TECHNICAL FIELD

The present invention relates generally to medical devices and in particular to a an improved display interface and method of operation for a medical device system that more efficiently facilitates interaction with a user.

BACKGROUND OF INVENTION

Implantable cardiac defibrillators (ICDs) are well established therapeutic devices for treating patients who have experienced one or more documented episodes of hemodynamically significant ventricular tachycardia or ventricular fibrillation. Since their clinical inception more than two decades ago, ICDs have evolved from basic to sophisticated electronic devices that provide physicians with a variety of clinically useful functions with which to treat patients.

Presently, even the most basic of ICDs typically has more than one tachycardia detection criterion, tiered therapy which combines bradycardia support pacing with various antitachycardia pacing modes, low-energy cardioversion, defibrillation, and data logging capabilities. The data logging capabilities within ICDs have become increasingly important, since the amount of data required for the ICDs operation increases proportionally with the increase in ICD functions. Efficiently processing this large amount of data has become possible with the incorporation of microprocessors and memory within the ICD.

Even with the advances in ICD data logging and processing capabilities, arrhythmia event recording capabilities have been limited, making it difficult to verify the adequacy and efficacy of arrhythmia detection and therapy settings. Furthermore, ICDs have been designed to record electrocardiogram and diagnostic channel data which can indicate to the physician the ICDs behavior during multiple tachyarrhythmic episodes. These ICDs also include arrhythmic event counters which log the number of episodes detected and the success or failure of each programmed therapy. Moreover, monitoring capability in some ICDs allow for recording of electrocardiogram waveforms, which can assist the physician in assessing the efficacy of the implanted ICD.

Once an ICD has been implanted, the physician interacts with the ICD through a clinical programmer. The clinical programmer is used to establish a telemetric link with the implanted ICD. The telemetric link allows for instructions to be sent to the electronic circuitry of the ICD and clinical data regarding the occurrence and treatment of a patient's cardiac arrhythmias and the ICD's operation to be sent from the electronic circuitry of the ICD to the clinical programmer. The typical programmer is a microprocessor-based unit that has a wand for creating the telemetric link between the implanted ICD and the programmer, and a graphics display screen that presents a patient's recorded cardiac data and ICD system information to the physician.

As the amount of cardiac data recorded by ICDs increases with each new generation of ICD, manufacturers and clinicians alike are becoming more sensitive to the role that time-efficient programming and data interpretation plays in the physician's clinical visit with the patient. As ICDs become increasingly complex, the interpretation of recorded arrhythmic episodes and the programming of the ICD can be challenging and time-consuming tasks for some users.

Therefore, a need exists for improved ICD and programmer technology that facilitates the identification of relevant information regarding the patient's clinical status. There is a need in the art for a system that helps the user quickly and efficiently interact with the ICD and programmer including programming the IDC, viewing cardiac data and assessing the patient's current status.

SUMMARY OF THE INVENTION

The present disclosure describes a medical device system having an improved interface and method of operation that more efficiently facilitates the interaction with a user. In one embodiment, the invention is directed toward a medical device system and method of storing cardiac data indicative of a plurality of arrhythmic episodes, displaying a plurality of user input mechanisms in a graphical, hierarchical arrangement on a display screen of a medical device programmer unit such that each input mechanism corresponds to subset of the episodes having a common data characteristic. When one of the input mechanisms is selected by a user, detailed information regarding the corresponding subset of the arrhythmic episodes is displayed. The common data characteristic used catagorize the episodes can be, for example, a zone of detection for or a type of arrhythmic episode.

In another embodiment, the invention is directed toward a medical device system and method that displays cardiac events in a histogram format on a display screen of a medical device programmer unit such that an axis of the histogram represents a range of rates. When a user selects a normal view the system scales the histogram as a function of all of the stored events. When the user selects a magnification view the system scales the histogram as a function of a subset of the events that are graphically depicted along a portion of the histogram rate axis. The portion of the histogram can be defined by an atrial tachyarrhythmia response (ATR) trigger rate or can correspond to one or more zones of detection.

In another embodiment, the invention is directed toward a medical device system and method that displays cardiac data on a display of a medical device programmer unit using a plurality of screens including a device activity screen that primarily presents information regarding a status of a patient. According to the invention, the medical device system defaults into displaying the device activity screen when the programmer is operated by a user and the patient is experiencing an arrhythmia.

In yet another embodiment, the invention is directed toward a medical device system and method that displays a summary screen having a plurality of sections. The summary screen associates and displays a shortcut link with each section such that a corresponding portion of the cardiac data is displayed in a detailed format when a user selects one of the shortcut links.

BRIEF DESCRIPTION OF DRAWING

In the drawings, where like numerals describe like components throughout the several views.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, programmatic, and structural changes may be made without departing from the spirit and scope of the present invention. The following detailed description is, therefore, not to be taken in a limiting sense and the scope of the present invention is defined by the appended claims and their equivalents.

The embodiments of the present invention illustrated herein are described as being included in an implantable cardiac defibrillator, which may include numerous pacing modes known in the art, and an external medical device programmer. However, the medical system and method of the present invention could also be implemented in an external cardioverter/monitor system as are known in the art. Also, the medical system and method of the present invention could also be implemented in an implantable atrial cardioverter-defibrillator, which may include numerous pacing modes known in the art. Furthermore, although the present invention is described in conjunction with an implantable defibrillator having a microprocessor based architecture, it will be understood that the implantable cardiac defibrillator (or other implanted device) may be implemented in any logic based, custom integrated circuit architecture, if desired.

Figure 1:
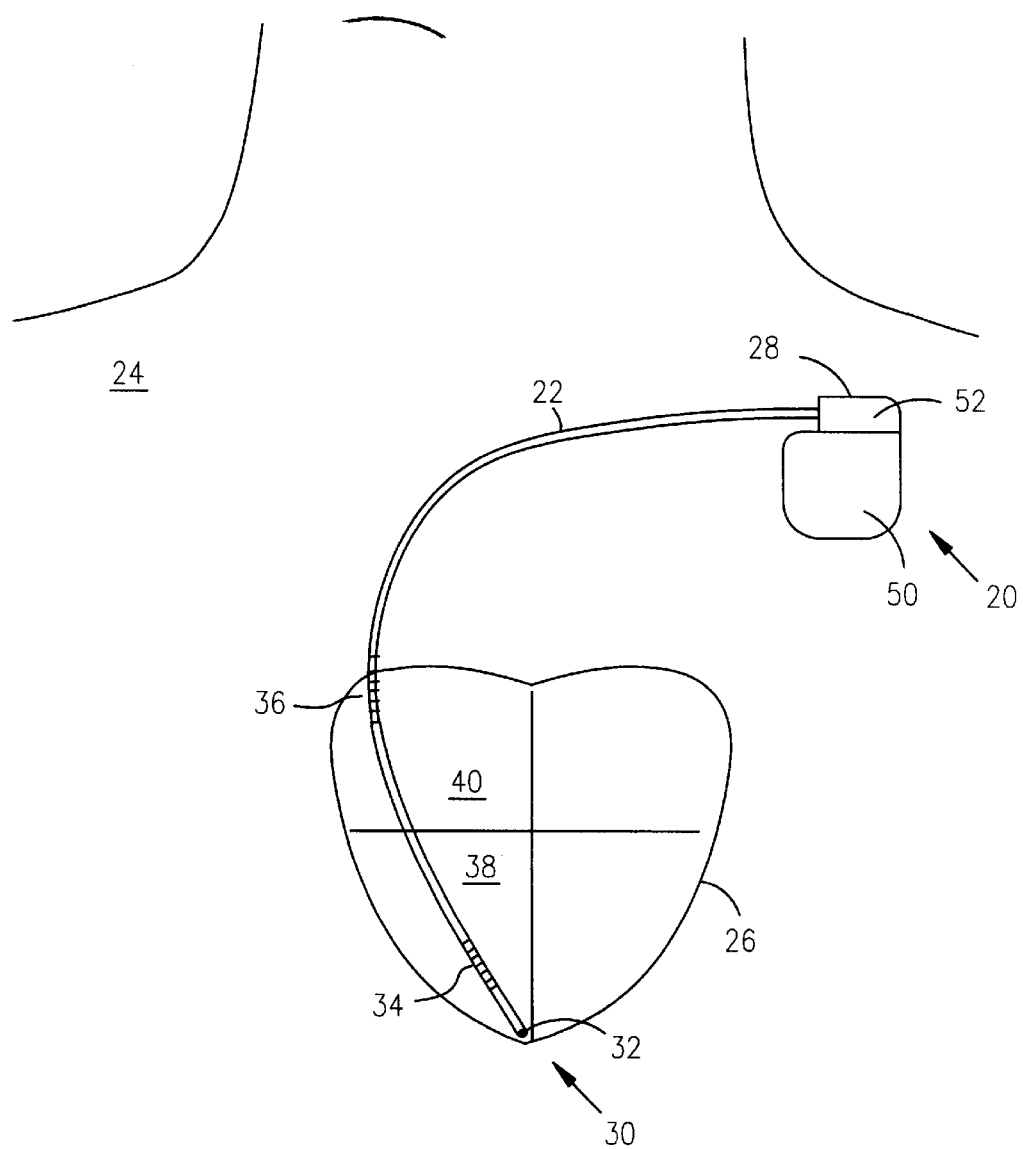
FIG. 1 is an embodiment of an implantable cardiac defibrillator implanted into a heart of a patient, from which portions have been removed to show detail.

Referring now to FIG. 1 of the drawings, there is shown one embodiment of a medical device system which includes an implantable cardiac defibrillator 20 electrically and physically coupled to at least one intracardiac catheter 22. In one embodiment, the intracardiac catheter 22 includes one or more pacing electrodes and one or more intracardiac defibrillation electrodes.

The intracardiac catheter 22 is implanted in a human body 24 with portions of the intracardiac catheter 22 inserted into a heart 26 to detect and analyze electric cardiac signals produced by the heart 26 and to provide electrical energy to the heart 26 under certain predetermined conditions to treat cardia arrhythmias, including ventricular fibrillation, of the heart 26.

In one embodiment, the intracardiac catheter 22 is an endocardial lead adapted to be releasably attached to the cardiac defibrillator 20. The intracardiac catheter 22 has an elongate body with a proximal end 28 and a distal end 30 and is shown as having a pacing electrode 32 located at, or adjacent, the distal end 30 of the intracardiac catheter 22. In one embodiment, the pacing electrode 32 is a tip electrode positioned at the distal end 30 of the intracardiac catheter 22. Alternatively, the pacing electrode 32 is an annular, or a semi-annular ring electrode positioned adjacent the distal end 30.

The intracardiac catheter 22 also includes one or more defibrillation electrodes. In one embodiment, the intracardiac catheter 22 has a first defibrillation electrode 34 and a second defibrillation electrode 36, where the first defibrillation electrode 34 and the second defibrillation electrode 36 are defibrillation coil electrodes as are known in the art. The first defibrillation electrode 34 is spaced apart and proximal from the pacing electrode 32, and the second defibrillation electrode 36 is spaced apart and proximal from the first defibrillation electrode 34 such that when the intracardiac catheter 22 is positioned within the heart 26 the pacing electrode 32 and the first defibrillation electrode 34 reside within a right ventricle 38 of the heart 26, with the pacing electrode 32 in an apex location within the right ventricle 38, and the second defibrillation electrode 36 is positioned within the right atrium chamber 40 of the heart 26 or a major vein leading to the right atrium chamber 40 of the heart 26.

Figure 2:
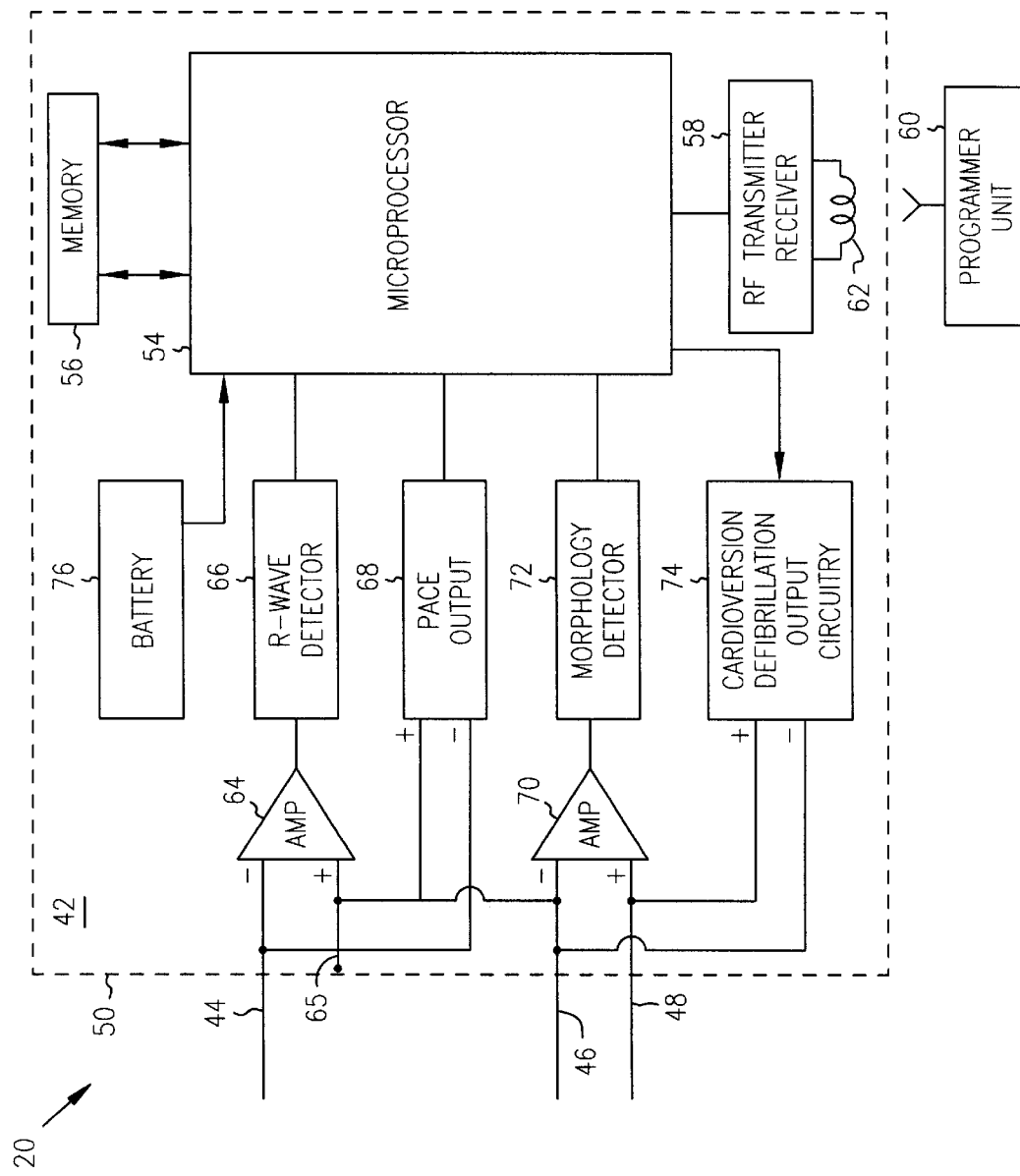
FIG. 2 is a block diagram of an implantable cardiac defibrillator according to one embodiment of the present invention.

Referring now to FIG. 2, there is shown an embodiment of a block diagram of a cardiac defibrillator 20. The cardiac defibrillator 20 includes electronic control circuitry 42 for receiving cardiac signals from a heart 26 and delivering electrical energy to the heart 26. The electronic control circuitry 42 includes terminals, labeled with reference numbers 44, 46, and 48 for connection to electrodes attached to the surface of the intracardiac catheter 22. The pacing electrode 32 is electrically connected to terminal 44 and to the electronic control circuitry 42 through an electrically insulated conductor provided within the elongate body of the intracardiac catheter 22. The first defibrillation electrode 34 and the second defibrillation electrode 36 are connected to terminals 46 and 48, respectively, and to the electronic control circuitry 42 through electrically insulated conductors provided within the elongate body of the intracardiac catheter 22.

In one embodiment, the electronic control circuitry 42 of the cardiac defibrillator 20 is encased and hermetically sealed in a housing 50 suitable for implanting in a human body. In one embodiment, titanium is used for the housing 50, however, other biocompatible housing materials as are known in the art may be used. A connector block 52 is additionally attached to the housing 50 of the cardiac defibrillator 20 to allow for the physical and the electrical attachment of the intracardiac catheter 22 and the electrodes to the cardiac defibrillator 20 and the encased electronic control circuitry 42.

The electronic control circuitry 42 of the cardiac defibrillator 20 is a programmable microprocessor-based system, with a microprocessor 54 and a memory circuit 56, which contains parameters for various pacing and sensing modes and stores data indicative of cardiac signals received by the electronic control circuitry 42.

A transmitter circuit 58 is additionally coupled to the electronic control circuitry 42 and the memory circuit 56 to allow the cardiac defibrillator 20 to communicate with a programmer unit 60. In one embodiment, the transmitter circuit 58 and the programmer unit 60 use a wire loop antenna 62 and a radio frequency telemetric link, as is known in the art, to receive and transmit signals and data to and from the programmer unit 60 and the electronic control circuitry 42. In this manner, programming commands or instructions are transferred to the microprocessor 54 of the cardiac defibrillator 20 after implant, and stored cardiac data pertaining to sensed arrhythmic episodes within the heart 26 and subsequent therapy, or therapies, applied to correct the sensed arrhythmic event are transferred to the programmer unit 60 from the cardiac defibrillator 20.

The embodiment of the cardiac defibrillator block diagram shows the pacing electrode 32 coupled to a sense amplifier 64. In an additional embodiment, the housing 50 of the cardiac defibrillator 20 is also coupled to the sense amplified 64 at 65 to allow for unipolar cardiac rate sensing between the pacing electrode 32 and the housing 50 of the cardiac defibrillator 20. The output of the sense amplifier 64 is shown connected to an R-wave detector 66. These components serve to sense and amplify the QRS waves of the heart, and apply signals indicative thereof to the microprocessor 54. Among other things, microprocessor 54 responds to the R-wave detector 66 by providing pacing signals to a pace output circuit 68, as needed according to the programmed pacing mode. Pace output circuit 68 provides output pacing signals to terminals 44 and 65, which connect to the pacing electrode 32 and the housing 50 of the cardiac defibrillator 20, for cardiac pacing.

The first defibrillation electrode 34 and the second defibrillation electrode 36 are coupled to a sense amplifier 70, whose output is connected to a cardiac morphology detector 72. These components serve to sense and amplify the QRS-waves of the cardiac cycle from the ventricular region of the heart 26, and apply signals indicative thereof to the microprocessor 54. In one embodiment, the cardiac morphology detector 72 includes an analog filter for filtering cardiac signal noise sensed by the electrodes. The cardiac signals are then bandlimited before arriving at an analog-to-digital filter. The cardiac signals are then A/D converted into a digital signal and subsequently received by the microprocessor 54. In an alternative embodiment, the cardiac signals are filtered through an analog peak detector to extract the maximum and minimum cardiac signal values for each sensed cardiac interval.

The microprocessor 54 responds to the cardiac signals sensed within the heart 26 using the intracardiac catheter 22 by providing signals to cardioversion/defibrillation output circuitry 74 to provide either cardioversion or defibrillation electrical energy to the heart 26 depending upon nature of the arrhythmia sensed by the cardiac defibrillator 20. Power to the cardiac defibrillator 20 is supplied by an electrochemical battery 76 that is housed within the cardiac defibrillator 20.

For each arrhythmic episode sensed, cardiac defibrillator 20 stores episode data in memory circuit 56 as illustrated in Table 1. Other arrhythmic episode data can also be recorded and stored in the memory circuit 56.

TABLE 1

| STORED DATA | DESCRIPTION |
| --- | --- |
| Number | Episode number stored in chronological order. |
| Time stamp | Date and time of the episode. |
| Type | The type of episode detected such as spontaneous, induced, pacemaker-mediated tachycardia (PMT), atrial tachyarrhythmia response (ATR), sustained or magnet activated. |
| Zone | The zone of detection which can be (VF), (VT), VT-1, Commanded, Accelerated. |

TABLE 1-continued

| STORED DATA | DESCRIPTION |
| --- | --- |
| Rate | The average rate of the episode in beats per minute. |
| Therapy | Therapy that was delivered to the patient prior to detecting including: none, one ATP, more than one ATP, one shock, more than one shock, ATP and shock. |
| Enhancement | Any detection enhancement criteria. |
| R-R Intervals | The time intervals between consecutively sensed R- waves for the episode. |
| EGMs | Data representing the sensed electrocardiogram signal such as a ventricular signal and an atrial signal. |
| Duration | The duration of the episode. |

Figure 3:
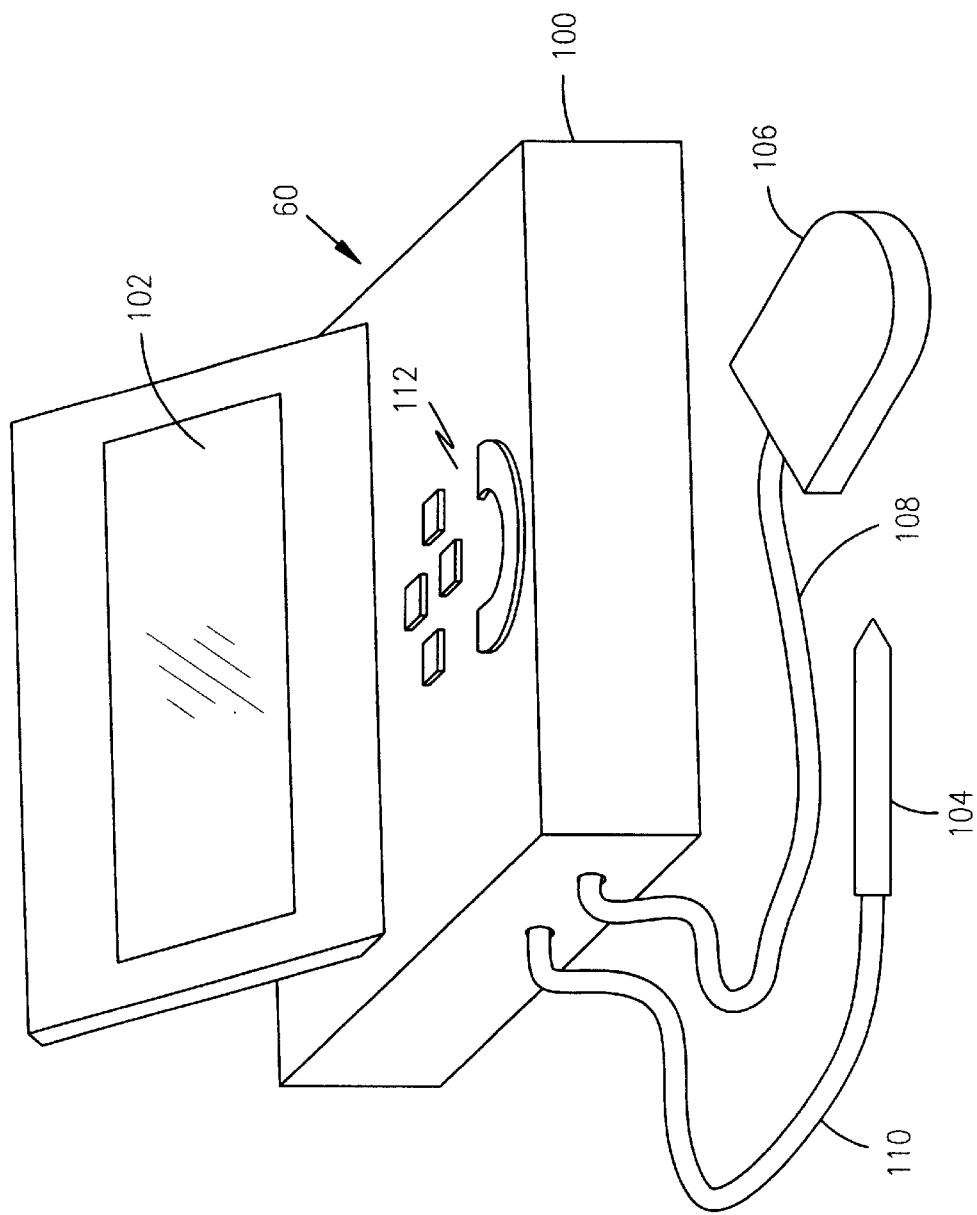
FIG. 3 is a perspective view of an external programming unit, according to one embodiment of the present invention, which is used for communicating with the implantable cardiac defibrillator of FIG. 1.

Referring now to FIG. 3, there is shown one embodiment of a medical device programmer 60 of the medical device system. As previously mentioned, one embodiment of programmer 60 for the implantable cardiac defibrillator 20 takes the form of an external controller as are known in the art. However, in an alternative embodiment, the medical device system is a completely external device such as an external cardioverting/defibrillator system as are known in the art, where the programmer unit is physically and electronically integrated into electronic control circuitry similar to the electronic control circuitry 42 of the cardiac defibrillator 20. An example of this latter embodiment is for an external cardiac monitor and defibrillation unit, electrically connected to the heart by any combination of intracardiac catheters, epicardial electrodes and/or externally cardiac electrodes, all of which are known in the art.

FIG. 3 shows one embodiment of programmer 60 designed to be positioned external of the human body 24 for communicating with an implantable medical device, such as the cardiac defibrillator 20 from FIG. 1, via RF telemetry. Programmer 60 has programmer electronic circuitry, including a microprocessing unit and related circuitry, such as digital memory, which is coupled to a graphics display screen 102.

In one embodiment, programmer 60 comprises an outer housing 100 which is made of a thermal plastic or other suitable lightweight durable material. The graphics display screen 102 is disposed on the upper surface of housing 100. The graphics display screen 102 folds down into a closed position when programmer 60 is not in use, thereby reducing the size of programmer 60 and protecting the display surface of graphics display screen 102 during transportation and storage.

In an additional embodiment, the external programmer additionally has a floppy disk drive and a hard drive disposed within the housing. Air vents are provided at various points in the housing 100 so that an internal fan can circulate air within the housing 100 and prevent overheating of components therein.

Programmer 60 is shown with the graphics display screen 102 positioned in one of a plurality of possible open positions such that a display on the graphics display screen 102 is visible to a user situated in front of programmer 60. In one embodiment, the graphics display screen 102 is of a liquid crystal display (LCD). The graphics display screen 102 is operatively coupled to the electronic circuitry disposed with the housing 100 and is adapted to provide a visual display of graphics and/or data under control of the programmer electronic circuitry.

Programmer 60 further includes a user input device coupled to the electronic circuitry. In one embodiment, the user input device is the graphics display screen 102, which is provided with touch-sensitive capability, such that a user can interact with the programmer electronic circuitry by touching the display area on the graphics display screen 102 with a stylus 104, or even the user's finger. In one embodiment, the touch-sensitive graphics display screen is primary input for programmer 60. Programmer 60 further includes a programming head 106, which is place over a patient's body near the implant site of an implanted device, such as the cardiac defibrillator 20, in order to establish a telemetry link between the cardiac defibrillator 20 and programmer 60. The telemetry link between the cardiac defibrillator 20 and programmer 60 allows the electronic circuitry coupled to the graphics display screen to be coupled to the electronic control circuitry of the cardiac defibrillator 20. The programming head 106 is coupled to the electronic circuitry of programmer 60 and a receiver circuit for receiving signals from the transmitter circuit indicative of cardiac signals by a cable 108.

The stylus 104 used to interact with the touch-sensitive graphics display screen 102 is coupled to the programmer electronic circuitry within the housing 100 by a cable 110. Alternatively, programmer 60 may be equipped with a conventional computer "mouse"-type pointing device, rather than a stylus. In the absence of either a stylus or a mouse, on-screen cursor control for enabling user interaction with programmer 60 may be facilitated through cursor control keys 112 (arrow keys or the like) disposed on programmer 60.

Programmer 60 further includes a receiver circuit for receiving signals from the transmitter circuit indicative of cardiac signals. Through the telemetric contact with the cardiac defibrillator 20, programmer 60 is capable of capturing and storing recorded electrocardiogram data transmitted from the cardiac defibrillator 20 and displaying the electrocardiogram data on its graphics display screen 102.

Figure 4:
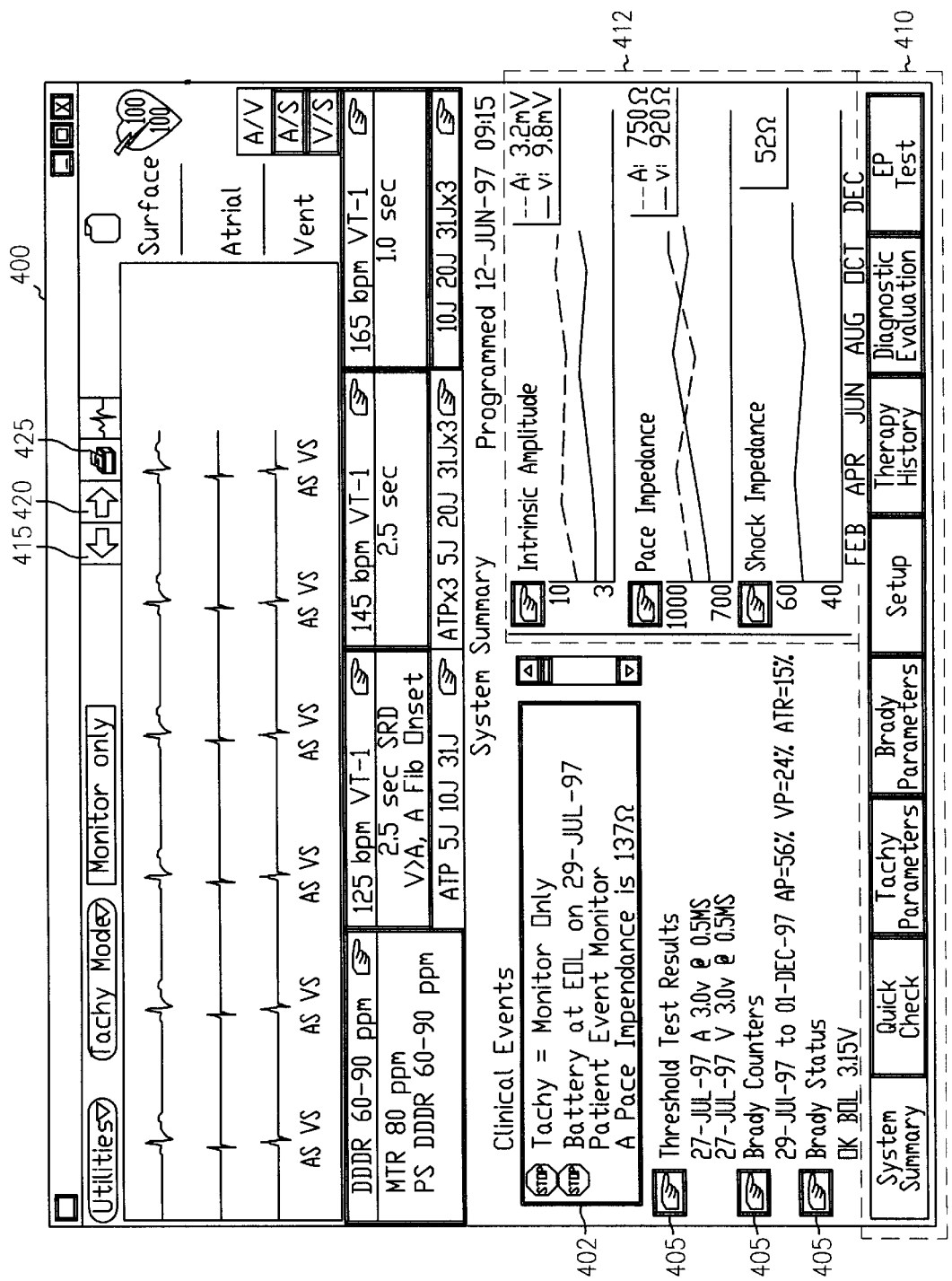
FIG. 4 illustrates a display screen presenting one embodiment of a system summary window that displays essential information regarding the status of programer, including the patients condition, and which acts as a home page for a user.

FIG. 4 illustrates display screen 102 presenting one embodiment of a system summary window 400 that displays all essential information regarding the status of programer 60 including the patient's condition. Upon initial interrogation, the programer 60 immediately defaults to the system summary window 400.

In order to facilitate interaction with a user, system summary window 400 acts as a home page for the user. System summary page 400 comprises several sections that display the following information: an abbreviated listing of the programmed parameters, a clinical events section 402 that lists a summary of the episodes and other device and system events that have occurred since last interrogation of cardiac defibrillator 20, threshold test results 404 that indicate current pulse thresholds, brady counters 406, a battery status 408 that indicates a current voltage and status of the battery, and a daily measurement graph section 412 that includes one or more daily graphs over a period of time such as the prior year. Examples of such graphs include an intrinsic amplitude graph, a pace impedance graph, and a shock impedance graph.

In addition to displaying high-level cardiac data in various sections, system summary window 400 associates and displays a shortcut link 405 for each section such that the user can quickly view detailed cardiac data by presented by specific display screens by clicking on the appropriate shortcut 405. Therefore, shortcut links 405 reduce the time required for the user to perform standard follow-up tests and reach the specific programming screens offered by programmer 60.

Navigation buttons 415 and 420 are another feature of system summary window 400 that results in time savings to the user. With the navigation buttons 415 and 420 the user is able to quickly move from one of the programming screens to another rather than having to memorize the sequence of screens that enabled him or her to reach the desired programming screen. Navigation button 415 allows navigation to screens that programmer 60 has previously displayed on display screen 120. Once the user has displayed previous screens, navigation button 420 allows a user to advance toward the most recently viewed screen. Thus, after programmer 60 displays a sequence of screens to the user based on user input, the user can traverse throughout the sequence using navigation buttons 415 and 420.

Another time saving feature of system summary window 400 is toolbox 410 where common programming tasks are grouped in a single section for the benefit of the user. In the embodiment illustrated in FIG. 4, eight tool buttons are grouped in order from left to right with the first being the most common programming task i.e., viewing the system summary window 400. The remaining common programming tasks include: a quick system check, tachy parameter programming, brady parameter programming, general programmer setup, viewing therapy history, diagnostic evaluation and electrophysiologic test. By grouping the most commonly occurring tasks together at the most accessible section of the system summary window 400, the user spends less time navigating through complex screens.

Yet another efficient and time saving feature of system summary window 400 is the ability to concurrently interrogate programmer 60 while printing episodes to a strip recorder. More specifically, when the user selects print button 425 programmer 60 will print the summary information to a strip recorder. Other cardiac information, such as the stored electrograms along with the corresponding intervals and markers, can also be printed from other screens. More specifically, the cardiac data will be printed in the background and batch printed in order to save time. Furthermore, according to the invention, programmer 60 can concurrently print episode data and interrogate defibrillator 20 to retrieve more episode data. The user does not need to wait until the print out is complete before moving to the next area of interest.

Figure 5:
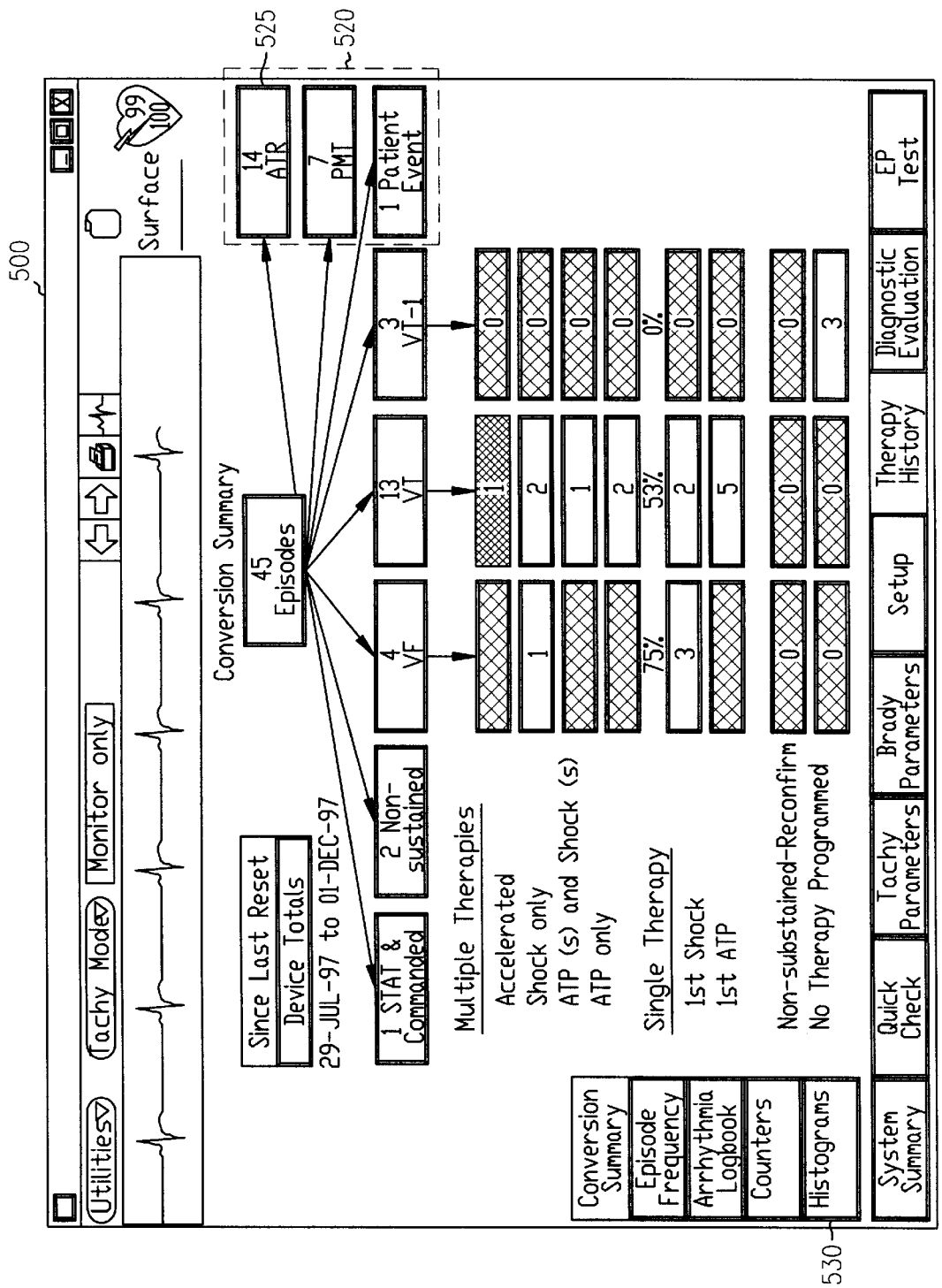
FIG. 5 illustrates a display screen presenting one embodiment of a conversion summary window that presents a graphical summary of the episodes that have occurred.

FIG. 5 illustrates display screen 102 presenting one embodiment of a conversion summary window 500 that presents a graphical summary of the episodes that have occurred. Conversion summary screen 500, displays a global summary of the episodes that have occurred in the patient. According to the invention, this global summary is displayed in a graphical, hierarchical fashion in order to give the user quick access to episodes of interest and the pertinent information of the episodes. Because the episodes are grouped by a common data characteristic, such as the zone of detection or type, there is no need for the user to individually select an episode in order to examine the details of an episode of interest.

Using date range selection 510, the user has the ability of displaying episodes that have occurred over the lifetime of cardiac defibrillator 20 or episodes that have occurred since cardiac defibrillator 20 was last reset. Section 520 of conversion summary window 500 displays, in a graphical, hierarchical arrangement, the episodes that have a common data characteristic such as having a common zone of detection or being of the same episode type. At the top level of the hierarchy 505, the total number of episodes is displayed. The second level of the hierarchy 520 displays a plurality of user input mechanisms that catagorize the episodes based on the common data type. For example, episodes may be organized by zone of detection such as VF (ventricular fibrillation), VT (ventricular tachycardia), VT-1 (ventricular tachycardia), commanded and accelerated. Also, episodes may be organized by type episode type such as, PMT (pacemaker-mediated tachycardia) and ATR (atrial tachyarrhythmia response).

When a particular user input mechanisms is selected, such as user input mechanisms 525, the user is presented a screen that displays specific details of the corresponding episodes, thereby saving the user time in navigating through several software screens in order to locate particular episodes of interest.

Figure 6A:
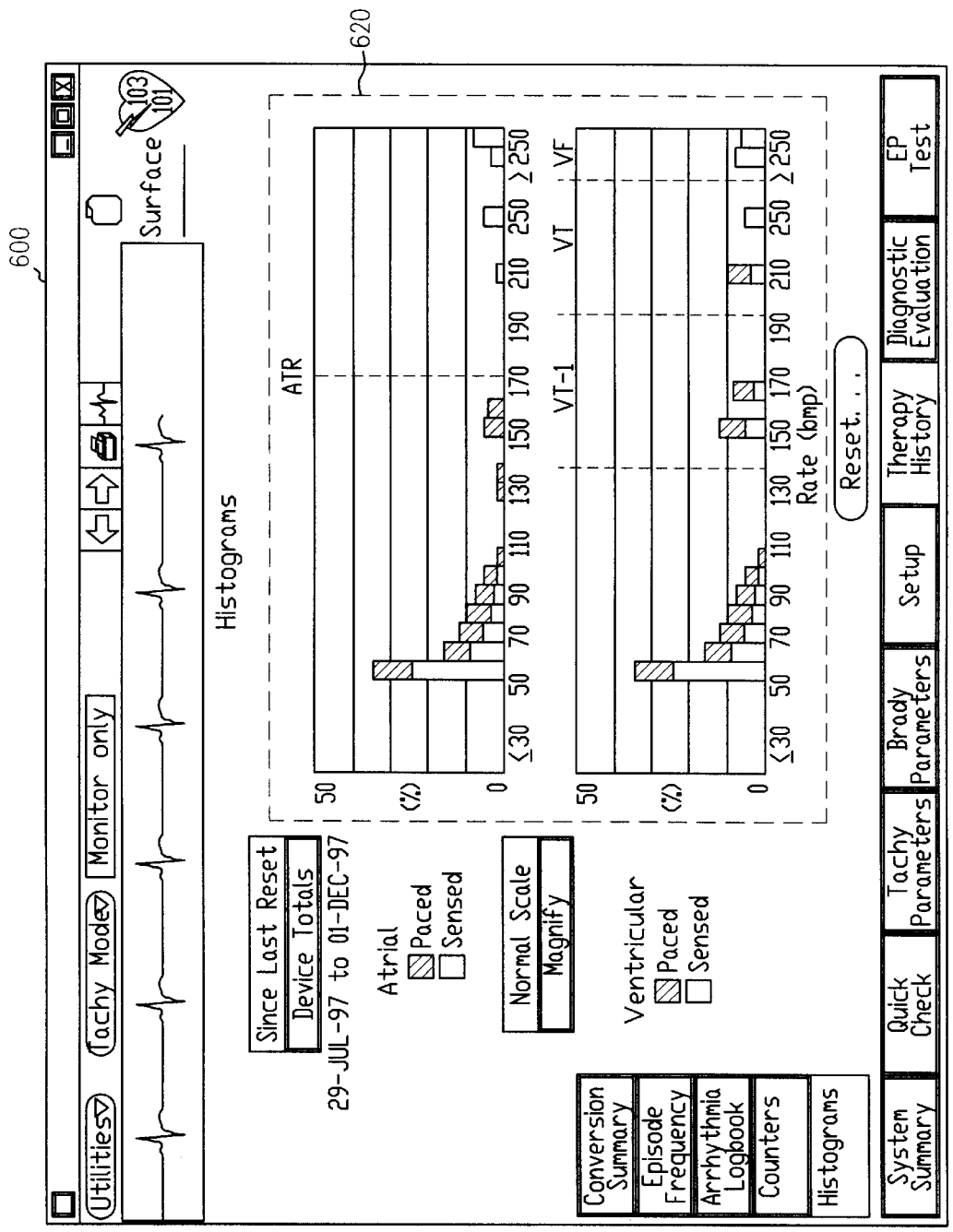
FIG. 6A illustrates a display screen presenting one embodiment of a histogram window graphically depicting cardiac event information.

Summary window 500 also includes histogram button 530 by which the user is able to view atrial and ventricular events in a histogram format. FIG. 6A illustrates display screen 102 presenting one embodiment of a histogram window 600 having a histogram display area 620 for presenting the information. Using date range input 605 the user is able to specify whether programmer 60 should display all of the events, only those events that have occurred since device 20 was reset or those events falling within a particular date range.

Within histogram display area 620, two histograms are illustrated an atrial event histogram and a ventricular event histogram. Both histograms have a horizontal axis that illustrates the rate of the event which, in this embodiment, ranges from 30 to 250 beats per minute (BPM). Magnification selection 610, however, controls the vertical axis and allows the user to select a normal view or a magnified view for histogram display area 620. In normal view, the histogram display area 620 presents the total number and percentage of paced and sensed events. In magnified view programmer 60 changes the vertical axes of histogram display area 620 from a percentage to an actual count and scales the vertical axis based on events falling within a portion of the horizontal axis. Thus, by selecting the magnification button 612 the user is able to easily view in enhanced detail the ventricular and atrial events that fall along the higher end of the horizontal axis.

Figure 6B:
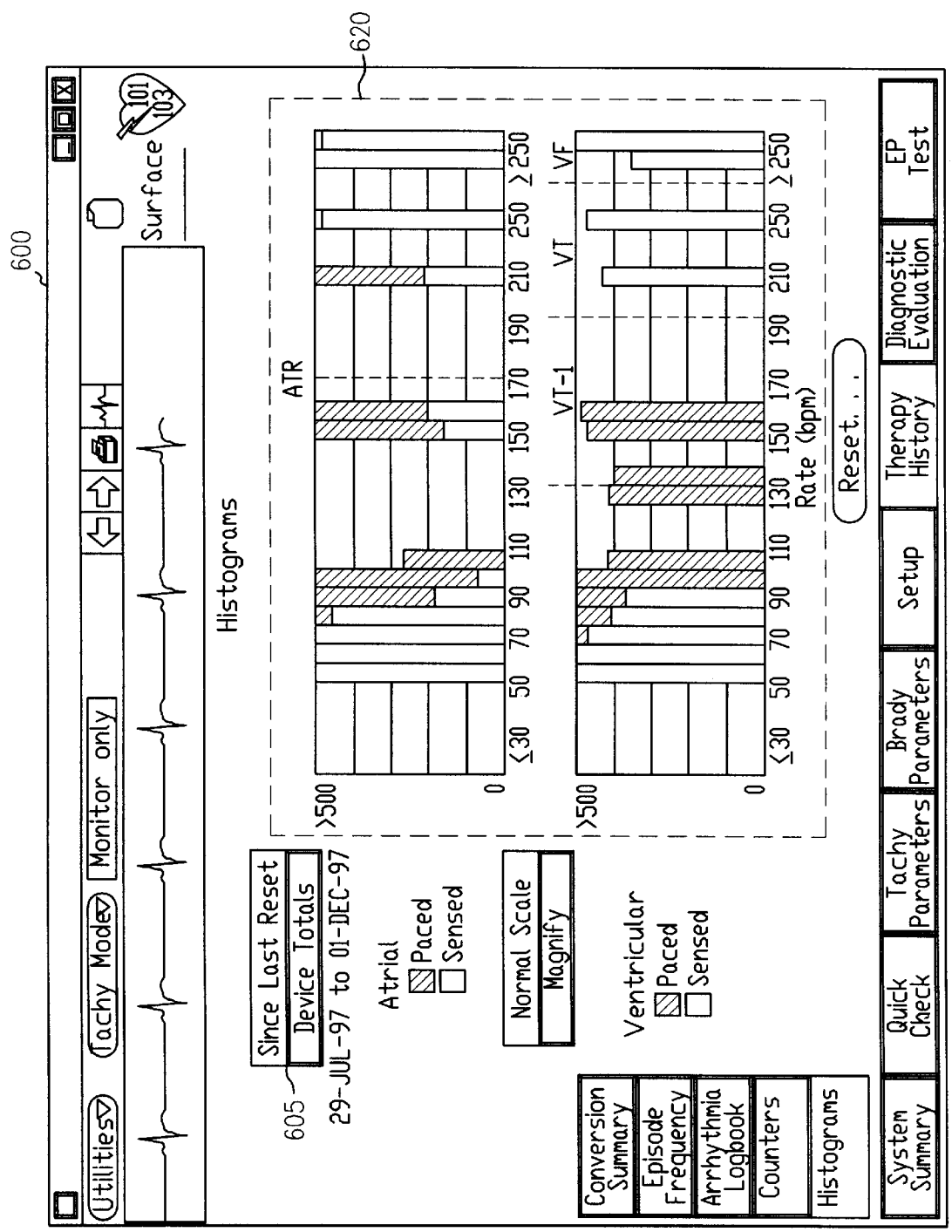
FIG. 6B illustrates a display screen presenting one embodiment of the histogram window of FIG. 6A where the user has elected to magnify a portion of the histogram.

FIG. 6B illustrates one embodiment of histogram window 600 where the user has elected to magnify a portion of the histogram. Here, the histogram display area 620, has magnified the event data. The magnification of each graph is based on the events above triggers 630 such that all magnified data above triggers 630 will be visible and will not exceed the top line of the graph. Events, however, below the triggers 630 may appear clipped during magnification. In the illustrated embodiment programmer 60 has scaled the vertical axis to display up to 500 events. This feature is useful because the events that typically occur at higher rates, and in higher zones, are much less frequent than those that occur at lower rates. Therefore, in conventional systems, the resolution of those higher rates is difficult to see by the user. By including an option that allows the user to magnify the small section of higher rates, the user can view the data clearer without permanently altering the display of other lower rates.

Figure 7:
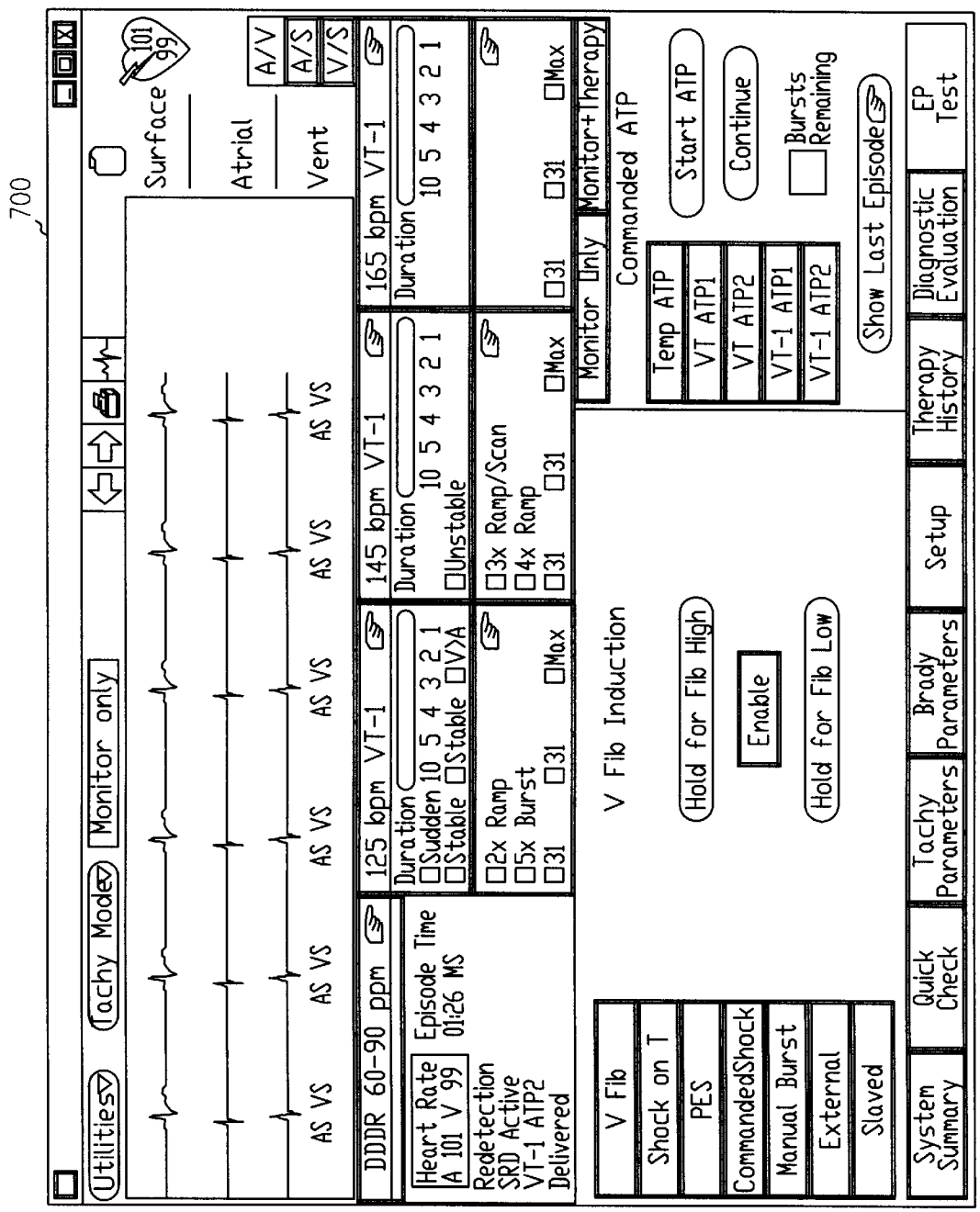
FIG. 7 illustrates a display screen presenting one embodiment of a device activity window that presents essential information regarding the patient.

Another inventive feature of programmer 60 is the ability to automatically default to a device activity screen anytime programmer 60 is interrogated and the patient is in an arrythmia at the time of interrogation. FIG. 7 illustrates display 102 presenting one embodiment of a device activity window 700 that displays essential information regarding the patient. In this manner, programmer 60 displays device activity window 700 and thereby allows for quick and efficient assessment of the status of the device and of the patient.

We claim:

1. A method comprising:

storing cardiac data indicative of a plurality of arrhythmic episodes;

displaying a plurality of user input mechanisms in a graphical, hierarchical arrangement on a display screen of a medical device programmer unit, where each input mechanism corresponds to a subset of the episodes having a common data characteristic; and displaying the corresponding subset of the arrhythmic episodes when one of the input mechanisms is selected by a user.

2. The method of claim 1, wherein the common data characteristic is a zone of detection.

3. The method of claim 2, wherein the common data characteristic is selected from the set of: VF (ventricular fibrillation), VT (ventricular tachycardia), and VT-1 (ventricular tachycardia), commanded and accelerated.

4. The method of claim 1, wherein the common data characteristic is a type of arrhythmic episode.

5. The method of claim 4 where the type is selected from the set of commanded, accelerated, PMT (pacemaker-mediated tachycardia) and ATR (atrial tachyarrhythmia response), non-sustained, and magnet activated.

6. A method comprising:

storing a plurality of arrhythmic episodes, wherein each arrhythmic episode has a corresponding zone of detection;

displaying a plurality of zone selection buttons on a display screen of a medical device programmer unit, where each button corresponds to one of the zones of detection; and displaying a subset of the arrhythmic episodes corresponding to one of the zone selection buttons selected by a user.

7. The method of claim 6, wherein displaying the zone selection buttons includes displaying within the each button a total number of episodes having a corresponding zone of detection.

8. The method of claim 6, wherein displaying the zone selection buttons includes displaying the zone selection buttons in a hierarchical arrangement.

9. The method of claim 8, wherein an episode total button is displayed as a top level of the hierarchy and each zone selection button is displayed within a second level of the hierarchy.

10. The method of claim 6, wherein the zone of detection is selected from the set of: VF (ventricular fibrillation), VT (ventricular tachycardia), VT-1 (ventricular tachycardia), commanded and accelerated.

11. A method comprising:

displaying cardiac data from a cardiac defibrillator on a display of a medical device programmer unit using a plurality of screens, where the screens are displayed in a viewing order based on navigation input from a user; and displaying a forward navigation button and a backward navigation button on the display to navigate forward and backward through the screens according to the viewing order.

12. A method comprising:

storing cardiac data corresponding to a plurality of arrhythmic episodes;

displaying a summary screen having a plurality of sections that present the cardiac data in a summary format including a graphical, hierarchical arrangement, wherein the summary screen presents a shortcut link for each section; and displaying a portion of the cardiac data in a detailed format when a user selects one of the shortcut links.

13. The method of claim 12, and further including displaying a toolbar on the summary screen such that the toolbar groups common programming tasks ordered from most commonly to least commonly used.

14. A method comprising:

storing a plurality of cardiac events, where each event has a corresponding rate;

displaying the cardiac events in a histogram format on a display screen of a medical device programmer unit, wherein the histogram has an axis representing a range of rates;

scaling the histogram as a function of all of the events when a user selects a normal view; and scaling the histogram as a function of a subset of the events that have a rate located along a portion of the histogram rate axis when the user selects a magnification view.

15. The method of claim 14, wherein the portion of the histogram is user-defined.

16. The method of claim 14, wherein the portion is defined by an ATR trigger rate.

17. The method of claim 14, wherein the portion corresponds to one or more zones of detection.

18. The method of claim 17, wherein the zones of detection include VF (ventricular fibrillation), VT (ventricular tachycardia) and VT-1 (ventricular tachycardia).

19. A method comprising:

displaying the cardiac data on a display of a medical device programmer unit using a plurality of different screens including a device activity screen that primarily presents information regarding a status of a patient; and when the medical device programmer is operated by a user, defaulting into displaying the device activity screen when the patient is experiencing an arrhythmia.

20. A computer-readable medium having computer-executable instructions to cause a computer to perform the method of:

storing cardiac data indicative of a plurality of arrhythmic episodes;

displaying a plurality of user input mechanisms in a graphical, hierarchical arrangement on a display screen of a medical device programmer unit, where each input mechanism corresponds to subset of the episodes having a common data characteristic; and displaying the corresponding subset of the arrhythmic episodes when one of the input mechanisms is selected by a user.

21. The computer-readable medium of claim 20, wherein the common data characteristic is a zone of detection.

22. The computer-readable medium of claim 20, further including computer-executable instructions to cause a computer to, where the common data characteristic is selected from the set of: VF (ventricular fibrillation), VT (ventricular tachycardia), and VT-1 (ventricular tachycardia).

23. The computer-readable medium of claim 20, wherein the common data characteristic is a type of arrhythmic episode.

24. A medical device system, comprising:

a cardiac defibrillator including electronic control circuitry for determining the occurrence of an arrhythmic episode of a heart;

a medical device programmer having programmer electronic circuitry coupled to an interactive display screen and the electronic control circuitry of the cardiac defibrillator, wherein the programmer electronic circuitry storing cardiac data indicative of a plurality of arrhythmic episodes, displays a plurality of user input mechanisms in a graphical, hierarchical arrangement on a display screen of a medical device programmer unit, where each input mechanism corresponds to subset of the episodes having a common data characteristic, and wherein the programmer electronic circuitry displays a corresponding subset of the arrhythmic episodes when one of the input mechanisms is selected by a user.

25. The medical device system of claim 24, wherein the common data characteristic is a zone of detection.

26. The medical device system of claim 25, where the common data characteristic is selected from the set of: VF (ventricular fibrillation), VT (ventricular tachycardia), and VT-1 (ventricular tachycardia), commanded and accelerated.

27. The medical device system of claim 24, wherein the common data characteristic is a type of arrhythmic episode.

28. The medical device system of claim 27, where the type is selected from the set of commanded, accelerated, PMT (pacemaker-mediated tachycardia), ATR (atrial tachyarrhythmia response), magnet activated and non-sustained.

29. A cardiac defibrillator, comprising a display screen and programmer electronic circuitry to receive cardiac data representing a plurality of stored arrhythmic episodes from the electronic control circuitry, and wherein the programmer electronic circuitry displays the cardiac data on the display screen using a plurality of different screens in a viewing order based on navigation input from a user, and further wherein the programmer electronic circuitry displays a forward navigation button and a backward navigation button on the display to navigate forward and backward through the screens according to the viewing order.

30. A medical device programmer, comprising a display screen and programmer electronic circuitry to receive cardiac data representing a plurality of stored arrhythmic episodes from the electronic control circuitry, wherein the programmer electronic circuitry presents a summary screen having a plurality of sections that present the cardiac data in a summary format including a graphical, hierarchical arrangement, wherein the summary screen displays a shortcut link for each section, and further wherein the electronic circuitry displays a portion of the cardiac data in a detailed format when a user selects one of the shortcut links.

31. A medical device programmer, comprising a display screen and programmer electronic circuitry to receive cardiac data representing a plurality of stored arrhythmic episodes from the electronic control circuitry, and wherein the programmer electronic circuitry displays a summary screen having a plurality of areas that summarize the cardiac data, wherein the summary screen has a toolbar that groups common programming tasks ordered from most commonly to least commonly used.

32. A medical device programmer, comprising a display screen and programmer electronic circuitry to receive cardiac data representing a plurality of stored cardiac events from the electronic control circuitry, wherein the programmer electronic circuitry displays the cardiac events in a histogram format on a display screen of a medical device programmer unit such that the histogram has an axis representing a range of rates, wherein when a user selects a normal view the electronic control circuitry scales the histogram as a function of all of the stored events; and further wherein when the user selects a magnification view the electronic control circuitry scales the histogram as a function of a subset of the events that have a rate located within a portion of the histogram rate axis.

33. The medical device programmer of claim 32, wherein the portion of the histogram is user-defined.

34. The medical device programmer of claim 33, wherein the portion is defined by an ATR trigger rate.

35. The medical device programmer of claim 33, wherein the portion corresponds to one or more zones of detection.

36. The medical device programmer of claim 35, wherein the zones of detection include VF (ventricular fibrillation), VT (ventricular tachycardia), and VT-1 (ventricular tachycardia).

37. A medical device programmer, comprising a display screen and programmer electronic circuitry to receive cardiac data representing a plurality of stored cardiac events from the electronic control circuitry, wherein the programmer electronic circuitry displays the cardiac data on a display of a medical device programmer unit using a plurality of different screens including a device activity screen that primarily presents information regarding a status of a patient, and further wherein the electronic control circuitry defaults into displaying the device activity screen when the medical device programmer is operated by a user the patient is experiencing an arrhythmia.

38. A method comprising:
   displaying a set of arrhythrnic episodes on a display of a medical device;
   printing a subset of the episodes to a strip recorder upon the request of a user; and
   concurrent with the printing of the subset, interrogating a cardiac defibrillator to receive cardiac data corresponding to the set of episodes that is being printed.

39. A method comprising:
   displaying a set of arrhythmic episodes on a display of a medical device;
   printing a subset of the episodes to a strip recorder upon the request of a user; and
   concurrent with the printing of the subset, interrogating a cardiac defibrillator to receive cardiac data.

* * * * *

UNITED STATES PATENT AND TRADEMARK OFFICE
CERTIFICATE OF CORRECTION

PATENT NO. : 6,415,175 B1  
DATED : July 2, 2002  
INVENTOR(S) : Conley et al.

Page 1 of 1

It is certified that error appears in the above-identified patent and that said Letters Patent is hereby corrected as shown below:

Title page,  
Item [56], References Cited, U.S. PATENT DOCUMENTS, delete "5,046,704" and insert -- 5,046,504 -- therefor.  
Insert -- 6,253,102      6/2001      Hsu, W., et al……….. 600/515 --.

Column 11,  
Line 56, delete "of 20" and insert -- of claim 20 --.

Signed and Sealed this

Seventeenth Day of December, 2002

JAMES E. ROGAN  
*Director of the United States Patent and Trademark Office*